United States Patent
Yamaguchi et al.

(10) Patent No.: US 7,326,055 B2
(45) Date of Patent: Feb. 5, 2008

(54) METHOD FOR BLEACHING TEETH AND BLEACHING AGENT FOR TEETH

(75) Inventors: Shin Yamaguchi, Tokyo (JP); Toshihiro Sekiguchi, Tokyo (JP); Keisuke Ikushima, Tokyo (JP); Shoji Akahane, Tokyo (JP); Koyu Aoki, Aichi-gun (JP); Takeshi Morikawa, Seto (JP); Takeshi Ohwaki, Nagoya (JP); Yasunori Taga, Nagoya (JP)

(73) Assignee: GC Corporation, Tokyo (JP)

( * ) Notice: Subject to any disclaimer, the term of this patent is extended or adjusted under 35 U.S.C. 154(b) by 0 days.

(21) Appl. No.: 11/434,871

(22) Filed: May 17, 2006

(65) Prior Publication Data

US 2006/0222604 A1 Oct. 5, 2006

Related U.S. Application Data

(62) Division of application No. 10/644,808, filed on Aug. 21, 2003, now abandoned.

(30) Foreign Application Priority Data

Aug. 27, 2002 (JP) ............................. 2002/247008

(51) Int. Cl.
*A61C 15/00* (2006.01)
(52) U.S. Cl. ...................... 433/216; 433/215
(58) Field of Classification Search ................ 433/216, 433/215
See application file for complete search history.

(56) References Cited

U.S. PATENT DOCUMENTS

| 6,835,688 B2 | 12/2004 | Morikawa et al. | |
|---|---|---|---|
| 6,951,463 B2 * | 10/2005 | Masuhara et al. | .......... 433/216 |
| 2004/0058149 A1 | 3/2004 | Zhou et al. | |
| 2004/0180008 A1 | 9/2004 | Yamaguchi et al. | |

FOREIGN PATENT DOCUMENTS

| EP | 1 192 933 | 4/2002 |
|---|---|---|
| EP | 1 205 244 | 5/2004 |
| JP | 1 192 933 | 4/2002 |
| JP | 1 457 200 | 9/2004 |

OTHER PUBLICATIONS

R. Asahi, et al. Science, vol. 293, XP-002254522, pp. 269-271, "Visible-Light Photocatalysis in Nitrogen-Doped Titanium Oxides", Jul. 13, 2001.

* cited by examiner

*Primary Examiner*—Cris Rodriguez
*Assistant Examiner*—Candice C Stokes
(74) *Attorney, Agent, or Firm*—Oblon, Spivak, McClelland, Maier & Neustadt, P.C.

(57) ABSTRACT

The invention relates to a method for bleaching teeth in which a solution of a nitrogen-doped titanium oxide powder is contacted on a surface of the teeth and the surface of the teeth is irradiated to bleach the surface of the teeth-by activating a photocatalytic reaction.

11 Claims, No Drawings

METHOD FOR BLEACHING TEETH AND BLEACHING AGENT FOR TEETH

CROSS-REFERENCE TO RELATED APPLICATIONS

This application is a divisional of U.S. application Ser. No. 10/644,808 filed Aug. 21, 2003, abandoned.

BACKGROUND OF THE INVENTION

1. Field of the Invention

The present invention relates to a method for bleaching teeth for removing pigments deposited on teeth (coloration and discoloration of teeth) by an action of a photocatalyst, and a bleaching agent for teeth suitable for carrying out the method for bleaching teeth. More specifically, it relates to a method for bleaching teeth by applying a bleaching agent for teeth having a photocatalytic activity on a surface of teeth, and irradiating the applied part with light to bleach the teeth based on a photocatalytic action thus produced, and a bleaching agent for teeth useful for carrying out the method for bleaching teeth comprising a solution containing nitrogen-deeped titanium oxide powder that produces a photocatalytic action upon irradiation with light.

2. Description of Conventional Art

It is generally considered that whiteness of teeth is an important factor of beautification, and there are strong demands for whitening teeth centrally in young women to produce increasing cases of desiring bleach of teeth. As a method for bleaching teeth, a method using a hydrogen peroxide aqueous ($H_2O_2$) solution has been generally practiced.

That is, such a bleaching method has been generally practiced as a method for bleaching teeth in that light and heat are applied to a hydrogen peroxide aqueous solution (concentration: about 30% by weight), in which gauze impregnated with a hydrogen peroxide aqueous solution is placed on a labial surface of teeth and irradiated with light by lamps from side to side for about 30 minutes. In this method, the lamps are made close to the teeth as much as possible, and a hydrogen peroxide aqueous solution is supplied by about 5 minutes to prevent the gauze from drying.

There are also a method of repeating such an operation six to eight times instead of the irradiation with light that a high frequency electric current is applied for 1 second with a spoon-shaped chip equipped on a high frequency electric cautery knife, and then the operation is suspended for 8 seconds, and a method of directly applying a solution (paste) formed by mixing a thickener with a hydrogen peroxide aqueous solution to teeth instead of impregnation into gauze. However, a hydrogen peroxide aqueous solution having a concentration exceeding 25% by weight is necessarily handled carefully due to the strong corrosion nature thereof.

Many other bleaching agents and bleaching methods using a hydrogen peroxide aqueous solution having a concentration of 30 to 35% combined with other equipments and other agents have been proposed, such as a bleaching method of using a mixed solution of hydrochloric acid, a hydrogen peroxide aqueous solution and diethyl ether as an agent (modified McInnes bleaching method), a method of using a paste formed by kneading powder of sodium perborate and a 30% by weight hydrogen peroxide aqueous solution as an agent (working bleach method), a bleaching agent for teeth formed by mixing a hydrogen peroxide aqueous solution and orthophosphoric acid and a bleaching method using the same (JP-A-8-143436), a bleaching agent formed by mixing a hydrogen peroxide aqueous solution and silicic anhydride and a method for bleaching vital teeth of coating the bleaching agent (JP-A-5-320033), and a dental bleaching composition containing a dental bleaching agent (such as urea hydrogen peroxide, hydrogen carbamide peroxide and carbamide peroxide) and a matrix material (such as carboxymethylene) and a method for bleaching teeth using the same (JP-A-8-113520). However, these methods involve the same problems as in the foregoing methods from the standpoint of the use of hydrogen peroxide in a high concentration. There is also a bleaching method using urea peroxide in a concentration of about 10% by weight, instead of a hydrogen peroxide aqueous solution, as an example of bleaching methods that have been practiced in the United States, but no sufficient results have been obtained.

As a bleaching agent and a bleaching method for teeth using no hydrogen peroxide aqueous solution in a high concentration as described in the foregoing, such a method for bleaching teeth is also proposed that uses titanium dioxide having a photocatalytic action and, depending on necessity, a hydrogen peroxide aqueous solution. However, the conventional bleaching method and bleaching agent using titanium dioxide has such a defect that they exhibit substantially no catalytic action with respect to visible light while they exhibit catalytic action with respect to ultraviolet light (generally having a wavelength of less than 380 nm) owing to the band gap of the titanium dioxide used (Eg for the anatase type titanium dioxide is 3.2 eV). Ultraviolet light is malefic to a human body and thus is not suitable for long-term irradiation in an oral cavity, and therefore, it has been demanded to develop a novel method for bleaching teeth and a novel bleaching agent for teeth using a substance that effectively exhibits a photocatalytic action by using a light source containing substantially no ultraviolet light, such as a dental light source.

SUMMARY OF THE INVENTION

An object of the present invention is to provide a method for bleaching teeth and a bleaching agent for teeth that exhibit high bleaching effect with visible light.

As a result of earnest investigations made by the inventors for solving the problems associated with the conventional techniques, it has been found that in the case where nitrogen-deeped titanium oxide as mentioned below is used, the absorption edge of the light absorption spectrum can be shifted to a long wavelength side in comparison to the conventional case using titanium dioxide, so as to exhibit a photocatalytic activity with light having a longer wavelength, whereby a method for bleaching teeth and a bleaching agent for teeth exhibiting a high catalytic activity with visible light can be obtained, and thus the invention has been completed. Examples of the nitrogen-deeped titanium oxide include those obtained in such a manner that titanium dioxide excellent in stability to water and acids is basically used as a photocatalytic substance, and it is subjected to one or more of these operations, i.e., a part of the oxygen site of titanium dioxide is substituted with a nitrogen atom as proposed in WO01/10552 by the inventors, a nitrogen atom is doped among the lattice of titanium dioxide crystals, and a nitrogen atom is doped on the crystalline boundaries of titanium dioxide.

That is, the present invention relates to a method for bleaching teeth comprising steps of applying a solution containing nitrogen-deeped titanium oxide powder on a surface of teeth, and irradiating the applied part with light to bleach the teeth based on a photocatalytic action thus produced, and it also relates to a bleaching agent for teeth comprising a solution containing nitrogen-deeped titanium oxide powder that is suitable for carrying out the method for bleaching teeth. It is preferred in the method for bleaching teeth that light thus irradiated is visible light. It is preferred in the bleaching agent for teeth that the nitrogen-deeped titanium oxide is a photocatalytic substance having a Ti—O—N structure having a titanium oxide crystalline lattice containing nitrogen and exhibiting a photocatalytic action in a visible light region, and in this case, it is further preferred that the nitrogen-deeped titanium oxide contains titanium oxide containing no nitrogen on the outer surface thereof, a surface of the nitrogen-deeped titanium oxide comprises a ceramic carried in an island form, needle form or a mesh form, and the surface of the nitrogen-deeped titanium oxide carries a charge separation substance. It is also preferred in the bleaching agent for teeth that the bleaching agent contains from 0.01 to 5% by weight of the nitrogen-deeped titanium oxide powder, the nitrogen-deeped titanium oxide powder has a specific surface area of 10 to 500 m$^2$/g, the solution contains water and/or an alcohol or a polyhydric alcohol as a solvent, the bleaching agent further contains 0.5 to 20% by weight of a thickener, the bleaching agent further contains 1 to 20% by weight of hydrogen peroxide, and the bleaching agent further contains 2 to 45% by weight of urea peroxide.

DESCRIPTION OF PREFERRED EMBODIMENTS

The bleaching agent for teeth according to the present invention has a solution containing nitrogen-deeped titanium oxide powder, and preferably a solution containing nitrogen-deeped titanium oxide in an amount of 0.01 to 5% by weight based on the total amount of the bleaching agent for teeth. The nitrogen-deeped titanium oxide powder is preferably a photocatalytic substance having a Ti—O—N structure having a titanium oxide crystalline lattice containing nitrogen and exhibiting a photocatalytic action in a visible light region as proposed in WO01/10552.

The nitrogen-deeped titanium oxide may be nitrogen-deeped titanium oxide shown in WO 01/10552 and can be produced by heat treating titanium oxide or hydrated titanium oxide in an atmosphere containing ammonia gas, an atmosphere containing a nitrogen gas, or a mixed atmosphere of a nitrogen gas and a hydrogen gas. The nitrogen-deeped titanium oxide can also be produced by mixing and agitating powder of titanium oxide and urea and then heating the mixture as shown in JP-A-2002-154823.

The nitrogen-deeped titanium oxide used in the present invention may contain titanium oxide containing no nitrogen on the outer surface thereof as shown in WO01/10552. According to the configuration, the hydrophilicity of the powder surface is improved, and the bleaching capability in wet conditions can be improved.

The nitrogen-deeped titanium oxide used in the present invention may comprise ceramics carried in an island form, needle form or a mesh form on the surface thereof, as shown in WO01/10552. Examples of the ceramics include at least one selected from alumina, silica, zirconia, magnesia, calcia, calcium phosphate, apatite, amorphous titanium oxide and a fluorine resin. The ceramics are liable to absorb stains deposited on teeth and can improve the bleaching capability.

As the nitrogen-deeped titanium oxide used in the present invention, such kinds of titanium dioxide may be used that are formed in such a manner that titanium of the nitrogen-deeped titanium oxide is substituted with at least one kind selected from vanadium, chromium, manganese, iron, cobalt, nickel, copper, zinc, ruthenium, rhodium, rhenium, osmium, palladium, platinum, iridium, niobium and molybdenum, or at least one of these elements is doped among the lattice of titanium dioxide crystals or on the crystalline boundaries of polycrystalline aggregates of titanium dioxide, as shown in JP-A-2001-205104. The absorption edge of the light absorption spectrum of these kinds of nitrogen-deeped titanium oxide can be shifted to a long wavelength side in comparison to the conventional case using titanium dioxide, so as to exhibit a photocatalytic activity with light having a longer wavelength.

The nitrogen-deeped titanium oxide used in the present invention may carry a charge separation substance on the surface thereof as shown in JP-A-2001-205103. Examples of the charge separation substance include at least one selected from Pt, Pd, Ni, $RuO_x$, $NiO_x$, $SnO_x$, $Al_xO_y$ and $ZnO_x$. The charge separation substance scavenges electrons or positive holes, and thus recombination of electrons and positive holes is effectively prevented. Therefore, the photocatalytic reaction can be carried out in a more effective manner to improve the bleaching capability.

In the case where the mixing amount of the nitrogen-deeped titanium oxide is less than 0.01% by weight, there is such a tendency that the effect as a photocatalyst is difficult to be obtained, and in the case where it is mixed in an amount exceeding 5% by weight, there is such a possibility that the bleaching agent for teeth is deteriorated in transparency, and thus the bleaching capability is reduced due to reduction in light transmittance. The mixing amount of the nitrogen-deeped titanium oxide is more preferably 0.01 to 2% by weight. The specific surface area of the nitrogen-deeped titanium oxide powder is preferably 10 to 500 m$^2$/g and nitrogen-deeped titanium oxide powder having a specific surface area less than 10 m$^2$/g has such a possibility of decreasing the catalytic activity, whereas there is a strong tendency that production, procurement and use of nitrogen-deeped titanium oxide powder having a specific surface area exceeding 500 m$^2$/g are difficult.

In the bleaching agent for teeth of the present invention, in order that the nitrogen-deeped titanium oxide powder is effectively made in contact with teeth, it is necessary that the bleaching agent for teeth is formed into a solution (including a paste) by using a solvent. The solvent for the solution is preferably water and/or an alcohol. Among these, water is the most preferred from the standpoint of reactivity of the nitrogen-deeped titanium oxide, and ethanol and a polyhydric alcohol are the most preferred from the standpoint of the application operation of the bleaching agent for teeth to teeth. In the polyhydric alcohol, glycerin, ethylene glycol, diethylene glycol, polyethylene glycol, propylene glycol, polypropylene glycol, sorbitol, mannitol and mixtures thereof are preferred since they are excellent in safety and good in affinity to teeth.

It is preferred that the bleaching agent of the present invention further contains a thickener in an amount of 0.5 to 20% by weight based on the total amount of the bleaching agent for teeth in order that the nitrogen-deeped titanium oxide is easily coated on teeth and is effectively stayed on the tooth surface. The mixing amount of the thickener of less than 0.5% by weight is difficult to obtain effect of mixing it, and mixing in an amount exceeding 20% by weight causes a possibility of deterioration in operationality on application to teeth due to a too high viscosity of the solution. The thickener used in the present invention may be those thickeners that have been used in the field of dentistry without particular limitation, and examples thereof include a synthetic additive, such as cellulose sodium glycolate, sodium alginate, alginic acid propylene glycol ester, sodium carboxymethyl cellulose, calcium carboxymethyl cellulose, starch sodium glycolate, starch sodium phosphate ester, sodium polyacrylate, methyl cellulose, hydroxypropyl cellulose and polyvinyl pyrrolidone, a natural thickener, such as guar gum, tara gum, tamarind seed gum, gum arabic, tragant gum, karaya gum, alginic acid, carrageenan, xanthan gum, gellan gum, curdlan, chitin, thitosan, and chitosamine, and an inorganic thickener, such as calcium carbonate, calcium silicate, magnesium silicate, magnesium sodium silicate, silica powder, amorphous hydrous silicic acid and fumed silica. It has been confirmed by experimentation that the suitable viscosity obtained with the thickener is preferably in a range from 0.3 to 10 Pa.s (at 25° C.). The mixing amount of the thickener for obtaining the viscosity in that range varies within the foregoing range depending on the species of the thickener. The mixing amount may be only about 0.5 to 8% for cellulose sodium glycolate or the like having a large thickening effect, whereas it is necessarily 15% or more for methyl cellulose or the like, and the suitable mixing amount is determined individually for the respective thickeners.

The bleaching agent for teeth according to the present invention may further contain hydrogen peroxide in an amount of 1 to 20% by weight based on the total amount of the bleaching agent for teeth in order to obtain bleaching effect by synergistic effect of the nitrogen-deeped titanium oxide and hydrogen peroxide in a low concentration. In the case where the mixing amount of hydrogen peroxide is less than 1% by weight, the effect of hydrogen peroxide is difficult to be obtained, and in the case where it is added in an amount exceeding 20% by weight, there is possible adverse affect to a living body due to corrosive nature of hydrogen peroxide. Upon irradiating the nitrogen-deeped titanium oxide powder with light, electrons and positive holes are generated, and they are reacted with hydrogen peroxide to form active oxygen. Active oxygen has larger oxidation power than ozone and can oxidatively decompose almost all organic substances to carbon dioxide gas. Even in the case of n-type semiconductor titanium oxide powder having a relatively large band gap, active oxygen having strong oxidation power is easily produced by irradiation with light upon using, for example, as a solution with a 3% hydrogen peroxide aqueous solution, and thus such factors as charge separation, mobility of electrons and positive holes, and reactivity with protons and hydroxyl groups, are increased in comparison to the sole use thereof, whereby the synergistic effect can be exerted correlatively with the oxidation action of the hydrogen peroxide aqueous solution itself.

The bleaching agent for teeth according to the present invention may further contain urea peroxide in an amount of 2 to 45% by weight based on the total amount of the bleaching agent for teeth in order to obtain stronger bleaching effect. In the case where the mixing amount of urea peroxide is less than 2% by weight, the effect of addition of urea peroxide is difficult to be obtained, and in the case where it is added in an amount exceeding 45% by weight, there is such a possibility that safety is lowered due to the urea peroxide.

The bleaching agent for teeth according to the present invention is a solution containing nitrogen-deeped titanium oxide, and for example, can be used in the form of solution as it is. In the case where hydrogen peroxide and/or urea peroxide is mixed, the mode of provision of them is not particularly limited, and for example, it is possible that the additional components are separately prepared and accompanied to the solution, and they are then mixed at a time of use. In addition, the bleaching agent for teeth according to the present invention may contain ordinary additives, such as a sweetener, a perfume and an antiseptic.

In the method for bleaching teeth according to the present invention, the solution containing nitrogen-deeped titanium oxide powder is applied to the surface of teeth. As one of the simplest methods for applying the solution on the surface of teeth, the solution containing nitrogen-deeped titanium oxide powder having a photocatalytic action as the bleaching agent for teeth is directly coated on teeth by using a brush or the like. Other examples thereof include such a method that cloth, paper, glass cloth, ceramic paper, organic gel or inorganic gel is impregnated with the bleaching agent for teeth and attached to the surface of teeth, followed by irradiating with light. Moreover, any appropriate methods can also be employed, such as a method, in which the bleaching agent for teeth is retained by a suitable carrier, such as a carrier in the form of a mouse guard, and it is outfit on teeth or a tooth raw to attach the solution to teeth.

Examples of a light source (lighting equipment) of light used in the present invention include an incandescent lamp, a fluorescent lamp, a halogen lamp, a xenon lamp, a mercury lamp and an UV lamp, and in particular, an LED (light emitting diode) and a semiconductor laser lamp (pen light) are preferred from the standpoint of safety, handiness and bleaching effect. The light to be irradiated is preferably that containing a large amount of light having a short wavelength, such as an ultraviolet ray, from the standpoint of generation of active oxygen by the photocatalytic action and the oxidation action thereof, but because an ultraviolet ray is harmful for a human body as causing inflammation and cancer, the use of visible light is preferred from the standpoint of safety with the use of violet and/or blue light having larger energy being most preferred.

The method for bleaching teeth according to the present invention can be carried out by repeating several times such an operation that the bleaching agent for teeth, which is the solution containing nitrogen-deeped titanium oxide having a photocatalytic action, is applied to the surface of teeth, which is then irradiated with light. The number of repetitions of the application and irradiation operations may be appropriately adjusted depending on the extent of discoloration of the teeth. The application and light irradiation operations may be generally carried out by applying a fresh solution on the teeth with an interval of about 15 to 20 minutes, and the interval and the frequency thereof may be appropriately determined depending on the conditions of the teeth and the formulation of the bleaching agent for teeth. The method for bleaching teeth according to the present invention is effective for bleaching both demyelinated teeth and myelinated teeth and exerts remarkable effect on bleaching the teeth in a simple and safe manner.

EXAMPLE

The invention will be specifically described with reference to the following examples, but the present invention is not construed as being limited thereto.

Production of Bleaching Agent for Teeth

As shown in Tables 1 to 13, nitrogen-deeped titanium oxide powder was mixed and dispersed in one or a plurality of water, ethanol, glycerin, polyethylene glycol (weight average molecular weight: 200) and sorbitol as a solvent, and then a small amount of a thickener (magnesium sodium silicate and silica fine powder (Aerosil R972, a trade name, produced by Nippon Aerosil Co., Ltd.)) was added thereto depending on necessity, so as to produce bleaching agents for teeth, which were then sealed in light shielding containers.

The following kinds of nitrogen-deeped titanium oxide powder were used.

(Powder A)

As shown in JP-A-2002-154823, commercially available titanium dioxide powder (ST-01, a trade name, produced by Ishihara Sangyo Kaisha, Ltd.) and urea were mixed and agitated, and then subjected to a heat treatment at 450° C. for 30 minutes to produce powder A having a specific surface area of 280 $m^2/g$.

(Powder B)

As shown in WO01/10552, commercially available titanium dioxide powder (ST-01, a trade name, produced by Ishihara Sangyo Kaisha, Ltd.) was subjected to a heat treatment in a mixed gas atmosphere of argon gas and ammonia gas at 600° C. for 3 hours to produce powder B having a specific surface area of 67 $m^2/g$.

(Powder A-Ap)

Apatite was carried on the surface of the powder A by the method shown in WO01/10552 to produce powder A-Ap.

(Powder B-Ap)

Apatite was carried on the surface of the powder B by the method shown in WO01/10552 to produce powder B-Ap.

(Powder A-Pt)

Platinum was carried on the surface of the powder A by the method shown in JP-A-2001-205103 to produce powder A-Pt.

(Powder B-Pt)

Platinum was carried on the surface of the powder B by the method shown in JP-A-2001-205103 to produce powder B-Pt.

In the case of a combination of such components that a metallic component (platinum in the examples) in the nitrogen-deeped titanium oxide and hydrogen peroxide were to start to react with each other immediately after mixing, the components were produced as separated to two or more portions, and the two or more portions of the bleaching agent for teeth were mixed immediately before application to teeth (Examples 19, 25, 26, 45, 51 and 52). In the case where the components were a combination of urea peroxide and water to be mixed, they were produced as separated to two or more portions since urea peroxide were to start to decompose by water immediately after mixing urea peroxide with water, and the two or more portions of the bleaching agent for teeth were mixed immediately before application to teeth (Examples 26 and 52). In the bleaching agent for teeth constituted of two or more portions in the examples, the same amounts (by weight) of the portions were mixed. The case using titanium dioxide powder (ST-01, a trade name, produced by Ishihara Sangyo Kaisha, Ltd.) as conventional titanium dioxide powder was designated as Comparative Example 1.

TABLE 1

(% by weight)

| | Example 1 | Example 2 | Example 3 | Example 4 | Example 5 |
|---|---|---|---|---|---|
| Powder A | 0.05 | 0.05 | 0.05 | 0.10 | 0.8 |
| Water | balance | balance | | balance | balance |
| Ethanol | | 40 | | | |
| Glycerin | | | balance | 40 | |
| Polyethylene glycol | | | | | 40 |
| Sodium magnesium silicate | 3 | 3 | | | |
| Silica fine powder | | | 5 | 5 | 5 |
| Total | 100 | 100 | 100 | 100 | 100 |

TABLE 2

(% by weight)

| | Example 6 | Example 7 | Example 8 | Example 9 | Example 10 |
|---|---|---|---|---|---|
| Powder A-Pt | 0.05 | 0.05 | 0.05 | 0.10 | 0.8 |
| Water | balance | balance | | balance | balance |
| Ethanol | 10 | 40 | | | 10 |
| Glycerin | | | balance | 40 | |
| Polyethylene glycol | | | 20 | | 40 |
| Sodium magnesium silicate | 3 | 3 | | | |
| Silica fine powder | | | | 5 | 10 |
| Total | 100 | 100 | 100 | 100 | 100 |

TABLE 3

(% by weight)

| | Example 11 | Example 12 | Example 13 | Example 14 | Example 15 |
|---|---|---|---|---|---|
| Powder A-Ap | 0.05 | 0.05 | 0.05 | 0.10 | 0.5 |
| Water | balance | balance | | balance | balance |
| Ethanol | | 40 | | 10 | |
| Glycerin | | | balance | 35 | |
| Polyethylene glycol | | | | | 35 |
| Sodium magnesium silicate | 10 | 5 | | | |
| Silica fine powder | | | 1 | 3 | 5 |
| Total | 100 | 100 | 100 | 100 | 100 |

TABLE 4

(% by weight)

| | Example 16 | Example 17 | Example 18 | Example 19 |
|---|---|---|---|---|
| Powder A | 0.05 | 0.05 | | 0.05 |
| Powder A-Pt | | | 0.05 | |

TABLE 4-continued (% by weight)

| | Example 16 | Example 17 | Example 18 | Example 19 | |
|---|---|---|---|---|---|
| Powder A-Ap | | | 0.05 | | |
| Water | balance | balance | balance | balance | balance |
| Hydrogen peroxide | 2.91 | 4.85 | 2.91 | | 2.91 |
| Sodium magnesium silicate | 3 | | 5 | 3 | 3 |
| Total | 100 | 100 | 100 | 100 | 100 |

TABLE 5

(% by weight)

| | Example 20 | Example 21 | Example 22 | Example 23 | Example 24 |
|---|---|---|---|---|---|
| Powder A | 0.05 | 0.10 | | | |
| Powder A-Pt | | | 0.05 | 0.10 | 0.8 |
| Urea peroxide | 10 | 15 | 5 | 20 | 15 |
| Ethanol | | | balance | | 5 |
| Glycerin | | balance | | 35 | balance |
| Diethylene glycol | | | 10 | balance | |
| Sorbitol | balance | | | | |
| Silica fine powder | 7 | | 10 | 5 | 12 |
| Total | 100 | 100 | 100 | 100 | 100 |

TABLE 6

(% by weight)

| | Example 25 | | | Example 26 | |
|---|---|---|---|---|---|
| Powder A-Pt | 0.05 | | | 1 | |
| Hydrogen peroxide | | 2.91 | | | 10 |
| Urea peroxide | 20 | | 30 | | |
| Water | | balance | | balance | |
| Ethanol | | 10 | 40 | | 35 |
| Glycerin | balance | | | balance | |
| Diethylene glycol | | | balance | | |
| Magnesium sodium silicate | | 3 | | 3 | 3 |
| Silica fine powder | 5 | | 7 | | 3 |
| Total | 100 | 100 | 100 | 100 | 100 |

TABLE 7

(% by weight)

| | Example 27 | Example 28 | Example 29 | Example 30 | Example 31 |
|---|---|---|---|---|---|
| Powder B | 0.2 | 0.2 | 0.2 | 0.5 | 1.0 |
| Water | balance | balance | | balance | balance |
| Ethanol | | 40 | | | |
| Glycerin | | | balance | 40 | |

TABLE 7-continued (% by weight)

| | Example 27 | Example 28 | Example 29 | Example 30 | Example 31 |
|---|---|---|---|---|---|
| Polyethylene glycol | | | | | 40 |
| Magnesium sodium silicate | 3 | 3 | | | |
| Silica fine powder | | | 5 | 5 | 5 |
| Total | 100 | 100 | 100 | 100 | 100 |

TABLE 8

(% by weight)

| | Example 32 | Example 33 | Example 34 | Example 35 | Example 36 |
|---|---|---|---|---|---|
| Powder B-Pt | 0.2 | 0.2 | 0.2 | 0.5 | 1.0 |
| Water | balance | balance | | balance | balance |
| Ethanol | 10 | 40 | | | 10 |
| Glycerin | | | balance | 40 | |
| Polyethylene glycol | | | 20 | | 40 |
| Magnesium sodium silicate | 3 | 3 | | | |
| Silica fine powder | | | | 5 | 10 |
| Total | 100 | 100 | 100 | 100 | 100 |

TABLE 9

(% by weight)

| | Example 37 | Example 38 | Example 39 | Example 40 | Example 41 |
|---|---|---|---|---|---|
| Powder B-Ap | 0.05 | 0.05 | 0.05 | 0.10 | 0.5 |
| Water | balance | balance | | balance | balance |
| Ethanol | | 40 | | 10 | |
| Glycerin | | | balance | 35 | |
| Polyethylene glycol | | | | | 35 |
| Magnesium sodium silicate | 10 | 5 | | | |
| Silica fine powder | | | 1 | 3 | 5 |
| Total | 100 | 100 | 100 | 100 | 100 |

TABLE 10

(% by weight)

| | Example 42 | Example 43 | Example 44 | Example 45 | |
|---|---|---|---|---|---|
| Powder B | 0.2 | 0.2 | | 0.2 | |
| Powder B-Pt | | | | 0.2 | |
| Powder B-Ap | | | 0.2 | | |
| Water | balance | balance | balance | balance | balance |
| Hydrogen peroxide | 2.91 | 4.85 | 2.91 | | 2.91 |

TABLE 10-continued (% by weight)

|  | Example 42 | Example 43 | Example 44 | Example 45 | |
|---|---|---|---|---|---|
| Sodium magnesium silicate | 3 |  | 5 | 3 | 3 |
| Total | 100 | 100 | 100 | 100 | 100 |

TABLE 11

(% by weight)

|  | Example 46 | Example 47 | Example 48 | Example 49 | Example 50 |
|---|---|---|---|---|---|
| Powder B | 0.2 | 0.5 |  |  |  |
| Powder B-Pt |  |  | 0.2 | 0.5 | 1.0 |
| Urea peroxide | 10 | 15 | 5 | 20 | 15 |
| Ethanol |  |  | balance |  | 5 |
| Glycerin |  | balance |  | 35 | balance |
| Diethylene glycol |  |  | 10 | balance |  |
| Sorbitol | balance |  |  |  |  |
| Silica fine powder | 7 |  | 10 | 5 | 12 |
| Total | 100 | 100 | 100 | 100 | 100 |

TABLE 12

(% by weight)

|  | Example 51 |  | Example 52 |  |
|---|---|---|---|---|
| Powder B-Pt | 0.2 |  | 2.0 |  |
| Hydrogen peroxide |  | 2.91 |  | 10 |
| Urea peroxide | 20 |  | 30 |  |
| Water |  | balance |  | balance |
| Ethanol |  | 10 | 40 |  | 35 |
| Glycerin | balance |  |  | balance |
| Diethylene glycol |  | balance |  |  |
| Magnesium sodium silicate |  | 3 | 3 | 3 |
| Silica fine powder | 5 | 7 |  | 3 |
| Total | 100 | 100 | 100 | 100 | 100 |

TABLE 13

(% by weight)

|  | Comparative Example 1 | Comparative Example 2 |
|---|---|---|
| Conventional titanium dioxide powder | 0.05 |  |
| Hydrogen peroxide |  | 35 |
| Water | balance | balance |
| Ethanol |  | 10 |
| Magnesium sodium silicate | 5 | 2 |
| Silica fine powder |  | 5 |
| Total | 100 | 100 |

(Method of Using)

(1) As a pretreatment, dental plaque, dental scale, tar and the like on the surface of the objective tooth were removed with an ultrasonic scaler.

(2) The surface of the tooth was cleaned with a rubber cup or the like in an ordinary method and then dried.

(3) A simple moisture prevention treatment was carried out.

(4) The bleaching agents for teeth of the examples and the comparative examples were coated on the surface of the tooth, and light irradiation was carried out by using a dental visible light irradiator (Labolight LVII, a trade name, produced by GC Corporation) The irradiation period was 5 minutes per once, and the distance from the surface of the tooth to the irradiator was about 1 cm.

(5) Application of a fresh bleaching agent for teeth and irradiation with light were repeated with an interval of 15 to 20 minutes.

(6) The effect of bleaching was evaluated in such a manner that colors of the tooth before and after bleaching were picturized with a video camera. The pictures thus obtained were presented to the patients, and evaluation was made in the following three grades.

+++: The patient was especially satisfied.

++: Bleaching effect somewhat satisfying the patient was obtained.

+: Bleaching effect was found, but discoloration somewhat remained, and the patient was not satisfied.

The results of the evaluation are shown in Table 14 below.

(Method of Using 2)

The surface of the tooth was cleaned in the foregoing manner. Paper ceramics (produced by Noritake Co., Ltd.) was impregnated with the bleaching agents for teeth in Examples 8, 17, 21, 34, 43 and 47, and attached to the surface of the tooth, followed by irradiating with visible light.

TABLE 14

|  | Site | Accumulated irradiation time (minute) | Effect |
|---|---|---|---|
| Example 1 | maxilla left 1 | 90 | +++ |
| Example 2 | maxilla left 2 | 100 | +++ |
| Example 3 | maxilla right 1 | 80 | +++ |
| Example 4 | maxilla left 3 | 90 | +++ |
| Example 5 | maxilla right 2 | 100 | ++ |
| Example 6 | mandible left 1 | 70 | +++ |
| Example 7 | mandible left 2 | 65 | +++ |
| Example 8 | maxilla right 3 | 80 | +++ |
| Example 9 | maxilla right 3 | 90 | +++ |
| Example 10 | maxilla left 2 | 80 | +++ |
| Example 11 | maxilla right 2 | 120 | +++ |
| Example 12 | mandible left 3 | 100 | +++ |
| Example 13 | mandible left 2 | 90 | ++ |
| Example 14 | mandible right 1 | 90 | +++ |
| Example 15 | mandible right 2 | 80 | +++ |
| Example 16 | mandible left 2 | 100 | ++ |
| Example 17 | mandible left 1 | 90 | ++ |
| Example 18 | maxilla left 1 | 120 | ++ |
| Example 19 | maxilla right 2 | 100 | ++ |
| Example 20 | mandible left 1 | 90 | ++ |
| Example 21 | mandible left 2 | 60 | +++ |
| Example 22 | maxilla right 3 | 50 | +++ |
| Example 23 | maxilla right 3 | 30 | +++ |
| Example 24 | maxilla left 2 | 55 | +++ |
| Example 25 | maxilla left 2 | 65 | +++ |
| Example 26 | maxilla right 1 | 70 | +++ |
| Example 27 | mandible left 2 | 100 | +++ |
| Example 28 | maxilla left 1 | 85 | +++ |
| Example 29 | mandible right 2 | 80 | +++ |

TABLE 14-continued

| | Site | Accumulated irradiation time (minute) | Effect |
|---|---|---|---|
| Example 30 | mandible left 3 | 95 | +++ |
| Example 31 | maxilla right 2 | 90 | ++ |
| Example 32 | maxilla left 1 | 80 | ++ |
| Example 33 | maxilla left 1 | 70 | +++ |
| Example 34 | maxilla right 2 | 90 | +++ |
| Example 35 | maxilla right 3 | 75 | +++ |
| Example 36 | maxilla left 1 | 75 | ++ |
| Example 37 | maxilla right 2 | 115 | +++ |
| Example 38 | mandible left 3 | 110 | +++ |
| Example 39 | maxilla left 1 | 70 | +++ |
| Example 40 | maxilla right 2 | 75 | +++ |
| Example 41 | mandible right 1 | 85 | +++ |
| Example 42 | mandible left 2 | 105 | ++ |
| Example 43 | maxilla left 1 | 95 | ++ |
| Example 44 | mandible left 3 | 110 | ++ |
| Example 45 | maxilla right 2 | 90 | ++ |
| Example 46 | mandible left 2 | 95 | ++ |
| Example 47 | mandible left 2 | 55 | +++ |
| Example 48 | maxilla right 2 | 45 | +++ |
| Example 49 | maxilla right 3 | 40 | +++ |
| Example 50 | mandible left 1 | 45 | +++ |
| Example 51 | maxilla left 2 | 50 | +++ |
| Example 52 | maxilla right 1 | 65 | +++ |
| Comparative Example 1 | maxilla right 3 | 120 | + |
| Comparative Example 2 | maxilla left 2 | 100 | ++ |

It was confirmed as apparent from the foregoing results that the method for bleaching teeth and the bleaching agent for teeth according to the present invention exerted high bleaching effect even with irradiation of visible light, and thus bleach of teeth could be carried out by using no hydrogen peroxide in a high concentration exceeding 30% by weight as in Comparative Example 2.

As described in the foregoing in detail, the method for bleaching teeth and the bleaching agent for teeth according to the present invention uses nitrogen-deeped titanium oxide, whereby the absorption edge of the light absorption spectrum can be shifted to a long wavelength side in comparison to the conventional case using titanium dioxide, so as to exhibit a photocatalytic activity with light having a longer wavelength. As a result, such a bleaching agent for teeth excellent in performance is provided that exhibits high bleaching effect even by using a dental visible light irradiator, which is generally used in dentistry, and such a method for bleaching teeth using the bleaching agent for teeth is also provided that can effectively bleach teeth with enjoying the effects of the bleaching agent. The nitrogen-deeped titanium oxide can be obtained in such a manner that titanium dioxide excellent in stability to water and acids is basically used as a photocatalytic substance, and it is subjected to one or more of these operations, i.e., a part of the oxygen site of titanium dioxide is substituted with a nitrogen atom, a nitrogen atom is doped among the lattice of titanium dioxide crystals, and a nitrogen atom is doped on the crystalline boundaries of titanium dioxide. Accordingly, the present invention greatly contributes to the field of bleach of teeth.

What is claimed is:

1. A method for bleaching teeth comprising
   contacting a solution that comprises a nitrogen-doped titanium oxide powder on a surface of the teeth; and
   irradiating the surface of the teeth in contact with the solution to bleach the surface of the teeth-by activating a photocatalytic reaction, wherein the nitrogen-doped titanium oxide powder comprises a titanium oxide that does not contain nitrogen on the outer surface thereof.

2. The method for bleaching teeth as claimed in claim 1, wherein irradiating includes exposing the surface of the teeth to a light in the visible light range.

3. The method as claimed in claim 1, wherein the nitrogen-doped titanium oxide has a Ti—O—N structure of a titanium oxide crystalline lattice containing a nitrogen.

4. The method as claimed in claim 1, wherein the nitrogen-doped titanium oxide powder is present in the solution in an amount of 0.01 to 5% by weight.

5. The method as claimed in claim 1, wherein the nitrogen-doped titanium oxide powder has a specific surface area of 10 to 500 $m^2/g$.

6. The method as claimed in claim 1, wherein the solution further comprises a thickener in an amount of 0.5 to 20% by weight.

7. A method for bleaching teeth comprising
   contacting a solution that comprises a nitrogen-doped titanium oxide powder on a surface of the teeth; and
   irradiating the surface of the teeth in contact with the solution to bleach the surface of the teeth-by activating a photocatalytic reaction, wherein the nitrogen-doped titanium oxide powder has a surface that comprises a ceramic carried in an island form, a needle form, or a mesh form.

8. A method for bleaching teeth comprising
   contacting a solution that comprises a nitrogen-doped titanium oxide powder on a surface of the teeth; and
   irradiating the surface of the teeth in contact with the solution to bleach the surface of the teeth-by activating a photocatalytic reaction, wherein the nitrogen-doped titanium oxide powder has a surface that carries a charge separation substance.

9. A method for bleaching teeth comprising
   contacting a solution that comprises a nitrogen-doped titanium oxide powder on a surface of the teeth; and
   irradiating the surface of the teeth in contact with the solution to bleach the surface of the teeth-by activating a photocatalytic reaction, wherein the solution comprises solution comprises water and polyhyrdric alcohol as a solvent.

10. A method for bleaching teeth comprising
    contacting a solution that comprises a nitrogen-doped titanium oxide powder and hydrogen peroxide in an amount of 1 to 20% by weight on a surface of the teeth; and
    irradiating the surface of the teeth in contact with the solution to bleach the surface of the teeth-by activating a photocatalytic reaction.

11. A method for bleaching teeth comprising
    contacting a solution that comprises a nitrogen-doped titanium oxide powder and urea peroxide in an amount of 2 to 45% by weight on a surface of the teeth; and
    irradiating the surface of the teeth in contact with the solution to bleach the surface of the teeth-by activating a photocatalytic reaction.

* * * * *